United States Patent [19]

Doubla et al.

[11] Patent Number: 5,122,245
[45] Date of Patent: Jun. 16, 1992

[54] PROCESS FOR THE SYNTHESIS OF "OXO" PRODUCTS BY THE PLASMA ROUTE AND INSTALLATION COMPRISING A PLASMA REACTOR USABLE IN THE PROCESS

[75] Inventors: Avaly Doubla, Cachan; Jacques Amouroux, Bures S/Yvette; Jean-Louis Brisset, Paris, all of France

[73] Assignee: Electricite De France, Paris, France

[21] Appl. No.: 527,036

[22] Filed: May 21, 1990

[30] Foreign Application Priority Data

May 24, 1989 [FR] France .................. 8906799

[51] Int. Cl.$^5$ .................................. C07C 1/00
[52] U.S. Cl. ....................... 204/168; 204/169; 204/170
[58] Field of Search ............. 204/165, 168, 170, 169; 568/429; 585/648, 953

[56] References Cited

U.S. PATENT DOCUMENTS

| | | | |
|---|---|---|---|
| 3,248,446 | 4/1966 | Pollock et al. | 585/536 |
| 4,183,871 | 1/1980 | Tavs et al. | 568/454 |
| 4,694,100 | 9/1987 | Shimizu et al. | 560/105 |
| 4,946,903 | 8/1990 | Gardella | 525/326.4 |

Primary Examiner—John F. Niebling
Assistant Examiner—Steven P. Marquis
Attorney, Agent, or Firm—Blakely, Sokoloff, Taylor & Zafman

[57] ABSTRACT

The present invention relates to a process for the synthesis of "oxo" products or their derivatives consisting of hydrocarbon compounds containing carbonyl and/or hydroxyl groups, characterized in that a hydrocarbon substrate containing an unsaturation, such as an alkene, is reacted with reactants consisting of a mixture of hydrogen and carbon monoxide, the reaction taking place after bringing the substrate into contact with the neutral activated species of the mixture of reactants activated to the plasma state.

In particular, the present invention relates to a process characterized in that an alkene is reacted to obtain a mixture containing the aldehyde and the alcohol resulting from the fixation on the double bond of the alkene of, respectively, a group

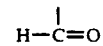

or its group

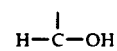

obtained by reduction, or only one of these two components by separating it from the mixture.

Finally, the present invention also relates to installations comprising a plasma reactor, in particular of the point-plane corona discharge type or of the high-frequency type, with an apparatus for chilling by a fluidized bed, usable in the process.

13 Claims, 11 Drawing Sheets

PROCESS FOR THE SYNTHESIS OF "OXO" PRODUCTS BY THE PLASMA ROUTE AND INSTALLATION COMPRISING A PLASMA REACTOR USABLE IN THE PROCESS

The present invention relates to a process for synthesis of hydrocarbon products of "oxo" type, that is to say having a substitution with a carbonyl group, or derivative products having, as substitution, hydroxyl groups resulting from the reduction of carbonyl groups. This synthesis of "oxo" products is obtained by reacting an unsaturated hydrocarbon substrate with a mixture of carbon monoxide and hydrogen In particular, the present invention relates to the synthesis of "oxo" products or their derivatives obtained by reacting an alkene with a mixture of carbon monoxide and hydrogen. The present invention also relates to installations comprising a plasma reactor usable in the process. The reaction of an unsaturated hydrocarbon substrate with a mixture of carbon monoxide and hydrogen leads to the synthesis of an aldehyde by fixation of a

group on the double bond of the alkene, but alcohols are also obtained because this aldehyde function is reduced to an alcohol function

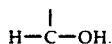

Products termed aldol condensation products resulting from the condensation of two aldehydes to give an aldol or hydroxyaldehyde, or an unsaturated aldehyde resulting from the dehydration of the said aldol, are also obtained. The presence of water resulting from this dehydration also makes it possible that the mixture of products obtained in the reaction, contains carboxylic acids or esters. Therefore, in the present application derivative products of "oxo" products are understood to be alcohols on the one hand and, on the other hand, the products deriving from aldol condensation, that is to say, in particular, aldols, unsaturated aldehydes, carboxylic acids and esters.

Several techniques are known for the preparation of these products, each using more or less specific variants (temperature, pressure, catalyst, etc.). These products are in general obtained under fairly severe conditions, in particular an elevated temperature of 100° to 200° C., elevated pressures of 150 to 200 atm and, finally, the presence of specific and active catalysts such as Cu, Ni, Co, Rh, Ru, etc. Moreover, the reaction kinetics are generally fairly slow and the treatment time several hours.

The aim of the present invention is to provide a process for the synthesis of "oxo" products or derivative products which takes place under milder, and thus more economic, conditions, in particular using less costly starting materials, with an improved yield and rate of reaction.

According to the present invention, this aim is achieved by making use of a reaction in plasma phase.

More precisely, the present invention relates to a process for the synthesis of "oxo" products or their derivatives consisting of hydrocarbon compounds containing carbonyl and/or hydroxyl groups, and especially carbonyl groups, characterized in that a hydrocarbon substrate containing a carbon unsaturation, such as an alkene, is reacted with reactants consisting of a mixture of hydrogen and carbon monoxide, the reaction taking place after bringing the substrate into contact with the neutral activated species of the mixture of reactants activated to the plasma state.

The reactive species $H_2$ and $CO$ are excited electronically by the plasma. In particular, a carbene(:CO) which, taking account of its acido-basic properties, leads to its fixation on the unsaturated sites of the hydrocarbon substrate, in particular an alkene, or on those of a cracking product of the said substrate. The carbene(:CO), taking account of its free radical properties, can in fact be responsible for the cracking of the hydrocarbon substrate.

Thus, under very mild synthesis conditions, "oxo" products are obtained, that is to say aldehydes resulting from the fixation of the group

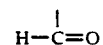

on the carbon unsaturation $C=C$ of the unsaturated substrate, such as the double bond of the alkene, but also the derivative products of these "oxo" products, that is to say alcohols resulting from the reduction of the aldehyde function, but also products termed aldol condensation products or derivatives of the latter as mentioned above, that is to say aldols, unsaturated aldehydes, carboxylic acids, esters, etc.

The substrate and the reactants are introduced into a plasma reactor at atmospheric pressure at an average temperature close to ambient temperature and without catalyst, the reactive species being excited solely by the plasma. The principle of the method is, in fact, a homogeneous catalysis reaction. The rate of reaction, that is to say the fixation of CO on the hydrocarbon substrate such as the alkene, is very rapid (for example 4 to 5 min treatment).

The advantages of the process according to the present invention are shown schematically in the table below.

| Conventional route | Plasma route |
| --- | --- |
| Elevated temperatures | Ambient temperature |
| 100 to 200° C. | 25 to 30° C. |
| Elevated pressures | Atmospheric pressure |
| 150 to 200 atm | 1 atm |
| Specific and active catalysts | Without catalysts |
| (Co, Rh, Ru, Ni, Cu, etc.) | activation due to the plasma |
| Slow kinetics | Rapid kinetics |
| Treatment time: | Treatment time: |
| a few hours | 5 to 10 min. |

A mixture of various compounds is obtained, which compounds can be separated by any method known to those skilled in the art, especially by distillation.

In particular, according to the present invention, an alkene can be reacted to obtain a mixture containing the aldehyde and the alcohol resulting from the fixation on the double bond of the alkene of, respectively, a group

or its group

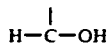

obtained by reduction, or to obtain only one of these two aldehyde or alcohol components, by separating it from the mixture, for example by distillation.

As has been seen above, the predominant products obtained are aldehydes and alcohols; however, by varying the various operating parameters of the reactor it is possible to obtain variable degrees of formation of these products. In particular, if the ratio of the CO/H2 volume flow rates is greater than 1, the aldehydes and alcohols will be obtained in an optimum manner; likewise, on the other hand, if the ratio of the CO/H2 volume flow rates is close to $\frac{1}{2}$ there will be preferential production of the products termed aldol condensation products.

Advantageously, according to the invention, the activation of the hydrogen/carbon monoxide mixture takes place in a plasma reactor, the substrate being brought into contact with the activated mixture outside the activation zone of the plasma. In fact, if the substrate is introduced into the activation zone and therefore is itself activated, the dielectric constant of the mixture is affected and becomes such that the establishment of an electric field sufficient for electronic excitation of the reactants and therefore for production of the synthesis necessitates having recourse to a high-voltage generator supplying a very much higher voltage.

Because of the ease with which it can be adapted to the specific problem of the oxo synthesis reaction under consideration, a plasma reactor of the point-plane corona discharge type is a reactor of choice in this process according to the invention.

An advantageous characteristic of the present invention then consists in that the point electrode of the plasma reactor of the corona discharge type is arranged in the reactor parallel to the plane electrode and the substrate is introduced into the reactor in the axis of the point and below the activation zone located between the point (brought to high voltage) and the plane (connected to earth). The configuration thus adopted is a configuration termed parallel, which has the advantage of separating the chemical reactivity of the charged species from that due to the neutral species activated by the discharge, which are responsible for the synthesis of "oxo" products such as the carbenes(:CO). This also enables as high as possible an electric field to be obtained without passing to arc operation.

Better yields are obtained when the point electrode is positively charged and the plane electrode connected to earth.

According to another characteristic, the carbon monoxide is introduced through a hollow electrode comprising the point, the hydrogen being introduced via the periphery of the reactor. Under these introduction conditions, all of the carbon monoxide is activated. If it were introduced via the periphery of the reactor, as is hydrogen, only the latter would be activated in a sufficient amount.

The present invention also relates to an installation, usable in the process according to the invention, comprising a plasma reactor of the point-plane corona discharge type, characterized in that it comprises one or more hollow point electrodes through which the reactor is fed with carbon monoxide gas, the point electrode being arranged parallel to the plane electrode, the hydrogen being introduced at the periphery of the reactor and the liquid hydrocarbon substrate being placed under the point in its axis at a point-substrate distance smaller than the point-plane distance.

In order to operate at a significant flow rate and to design an industrial installation of high tonnage, a variant of the process consists in making use of a thermal plasma reactor, in particular of the type comprising a plasma torch produced by high frequency, the CO+H2 mixture activated to the plasma state then being subjected to chilling through a bed of fluidized particles by a stream of hydrogen gas at a temperature of between 20° and 150° C., before, once cooled, being brought into contact with the substrate, which can be in liquid phase or vapour phase.

The process then consists in mixing a thermal plasma CO+H2 in a bed of solid particles fluidized by a stream of gas at a temperature lower than that of the plasma and in reacting the cooled activated mixture thus produced with the hydrocarbon substrate in order to form the "oxo" products.

Advantageously, the stream of gas is circulated below the fluidized bed through a tubular reactor in which the plasma reacts with the substrate circulating in counter-current.

The fluidized bed is of the gushing type.

The installation for carrying out this process therefore comprises a fluidized bed apparatus comprising a chamber containing means for the injection of the fluidization gas at the level of its base and means for exit of said gas and containing a mass of solid particles intended to form a fluidized bed, and a plasma torch adapted for injecting the plasma inside the chamber into the fluidized bed of particles. A tubular reactor connected to the outlet of said chamber is provided.

Advantageously, the plasma torch is connected at the level of a side wall of the chamber in such a way that the plasma is injected laterally into the fluidized bed.

The tubular reactor is advantageously of the packing column type in which the reaction takes place, the substrate circulating in counter-current to the flow of activated CO+H2 mixture.

Other characteristics and advantages of the present invention will become apparent in the light of the description which follows, referring to the drawings, in which:

FIG. 2 shows a variation in the transmission as a function of the wave number of hex-1-ene treated by the process according to the invention for two different distances; a) reference, b) d=10 mm; c) d2=17 mm (inter-electrode distance).

The operating conditions are:
I=50 μA
t=8.39 minutes
CO/H2=$\frac{1}{2}$

Figure 3:
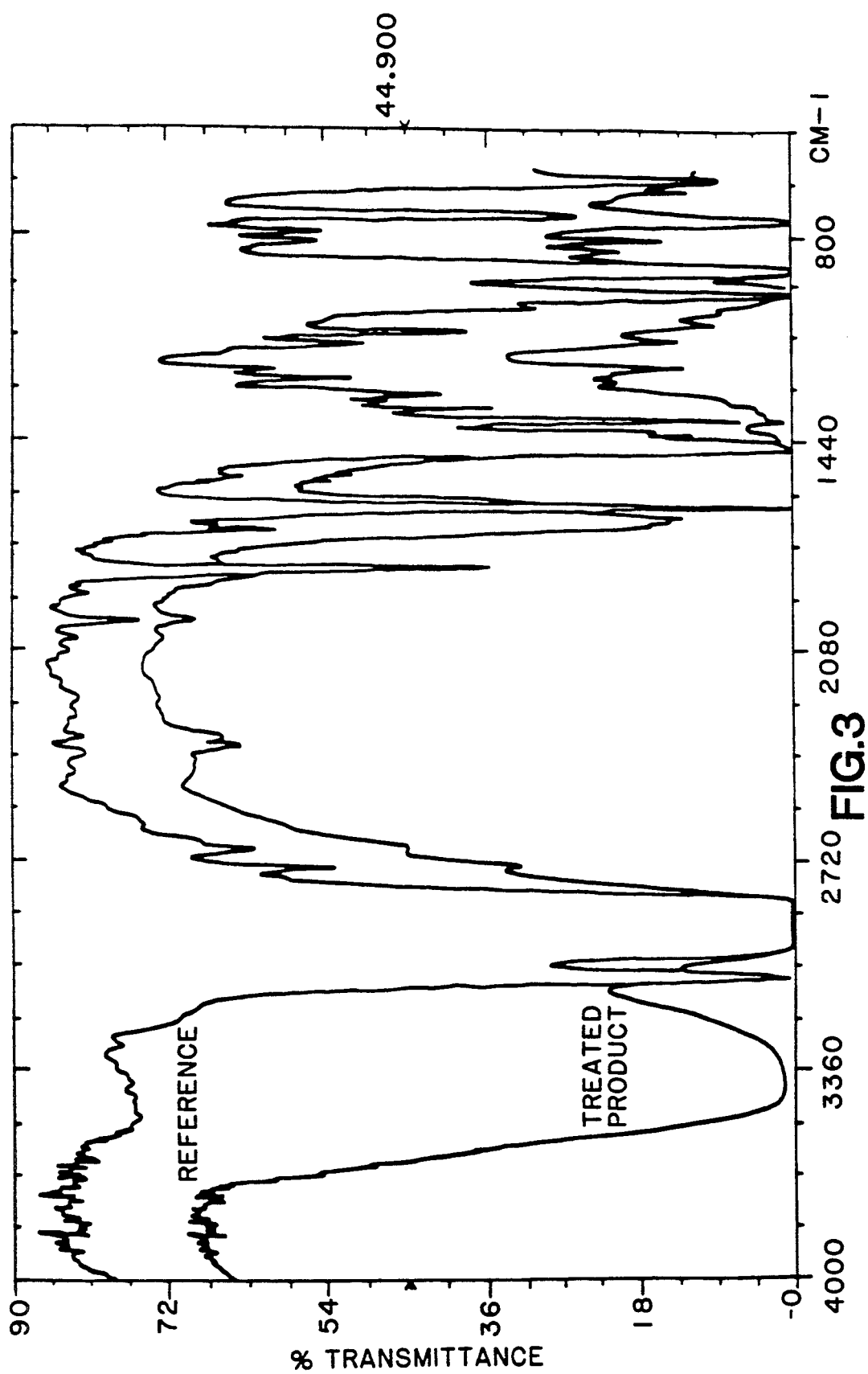

FIG. 3 shows the variation in the transmission as a function of the wave number of hex-1-ene (reference) and of the product obtained after treatment.

Figure 4:
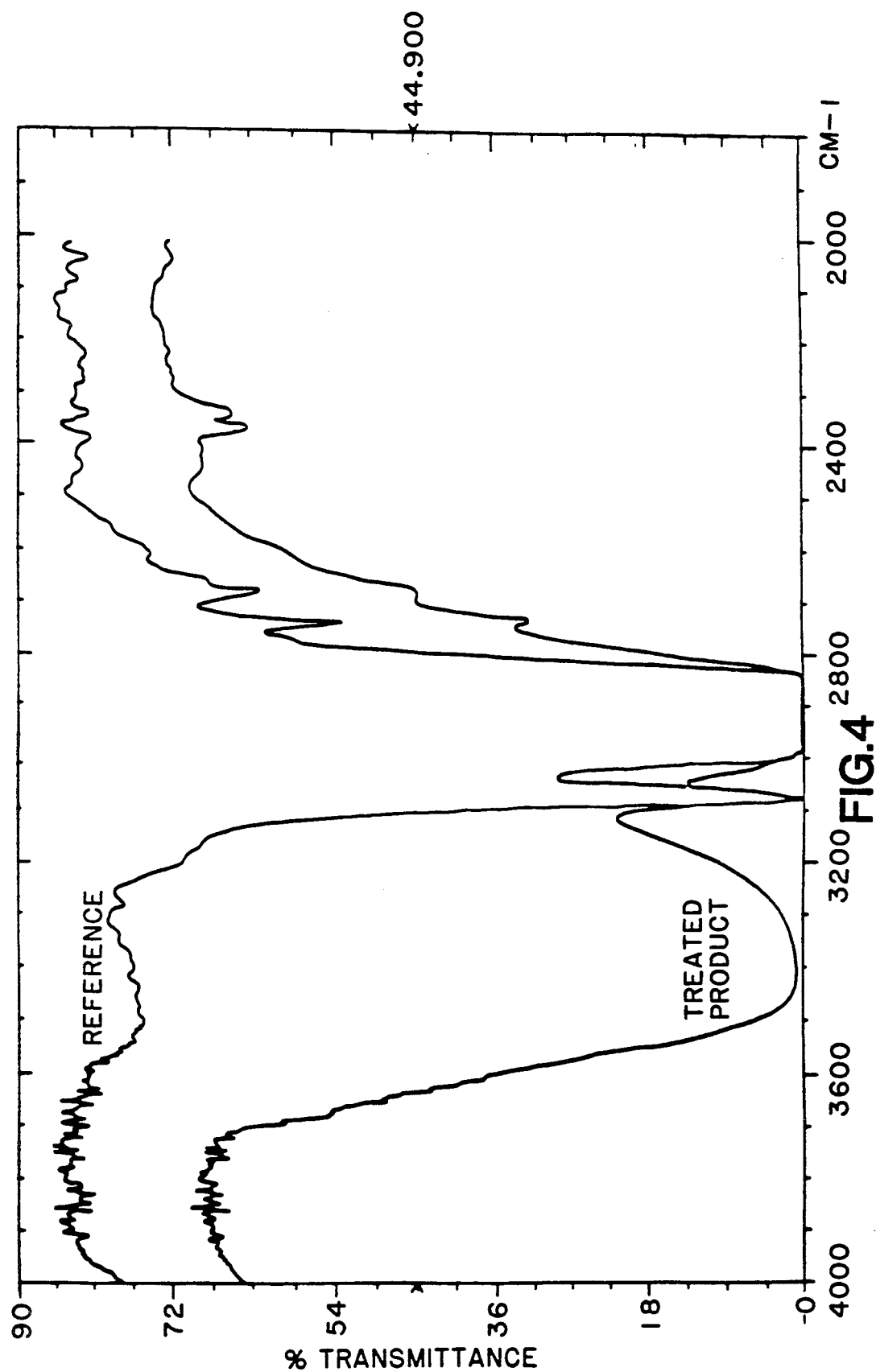

The operating conditions are:
$CO/H_2 = \frac{1}{2}$
$I = 50 \mu A$
$t = 8.00$ minutes
$V = 18.5$ kV
$d_2 = 13$ mm; $d_1 = 7$ mm FIG. 4 shows the variation in the absorption intensity of the —OH band of hex-1-ene (reference) and of the product obtained after treatment.

Figure 5:
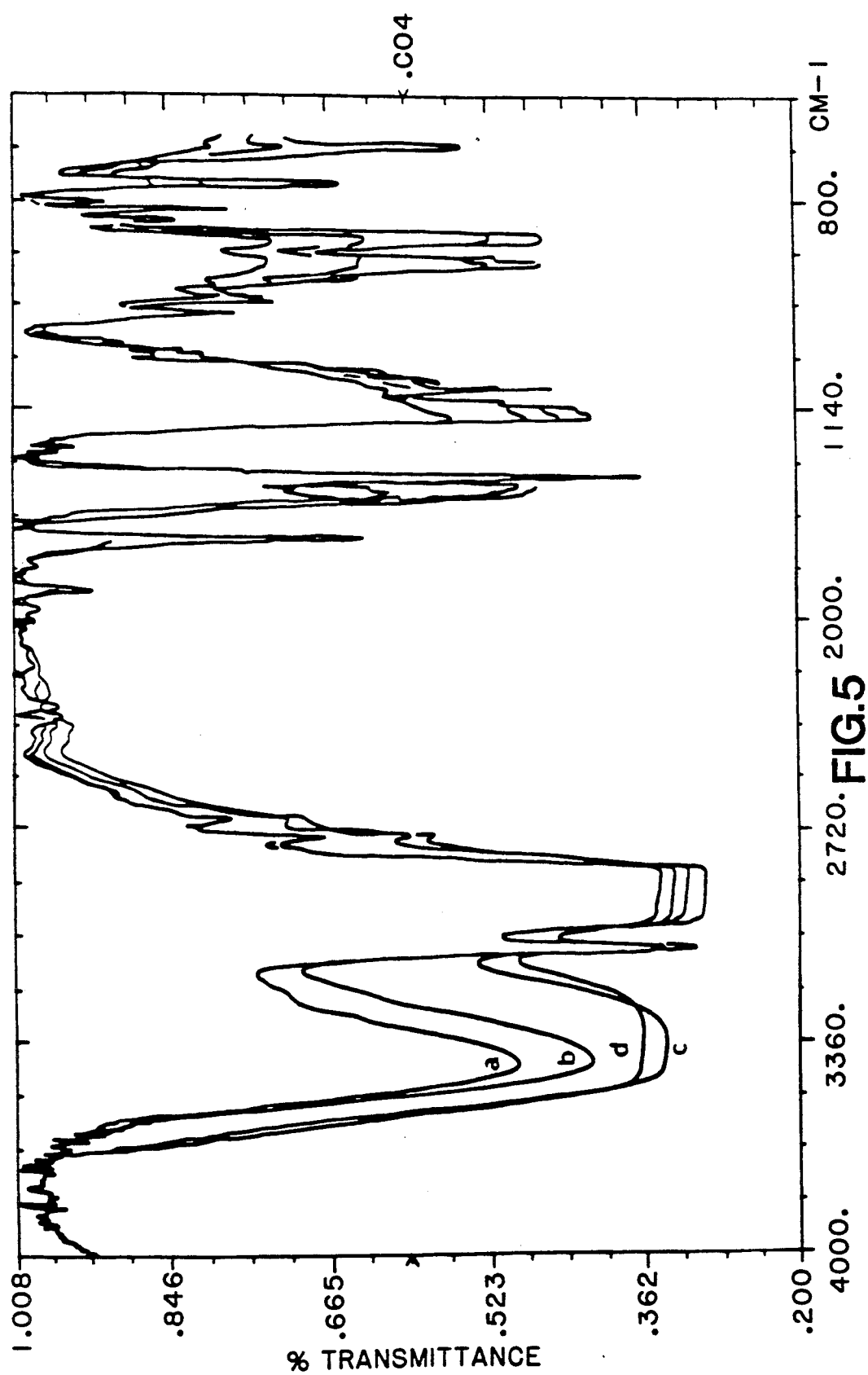

The operating conditions are:
$t = 8.39$ minutes
$I = 50 \mu A$
$V = 16$ kV
$d_2 = 17$ mm; $d_1 = 8$ mm
$CO/H_2 = \frac{1}{2}$ FIG. 5 shows the influence of the current intensity on the nature of the products formed (carbonyl and hydroxy compounds).

The operating conditions are:
$t = 10$ minutes
$V = 18.5$ kV
$d_2 = 10$ mm; $d_1 = 8$ mm
$CO/H_2 = \frac{1}{2}$
I variable: a) 20 $\mu A$; b) 50 $\mu A$; c) 80 $\mu A$; d) 100 $\mu A$.

Figure 6:
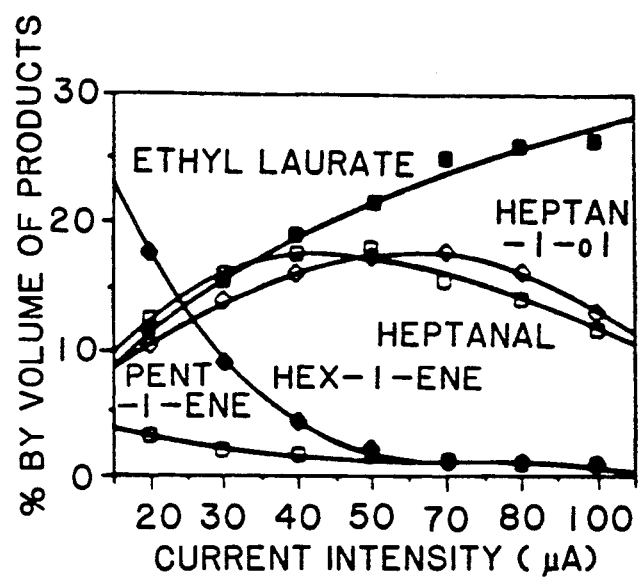

FIG. 6 shows, taking hex-1-ene as an example, the influence of the current intensity on the nature and the percentage of the main products obtained by GPC.

The operating conditions are:
$d_2 = 13$ mm; $d_1 = 7$ mm
time $t = 8$ minutes
$CO/H_2 = 1$ (ratio by volume)

Figure 7:
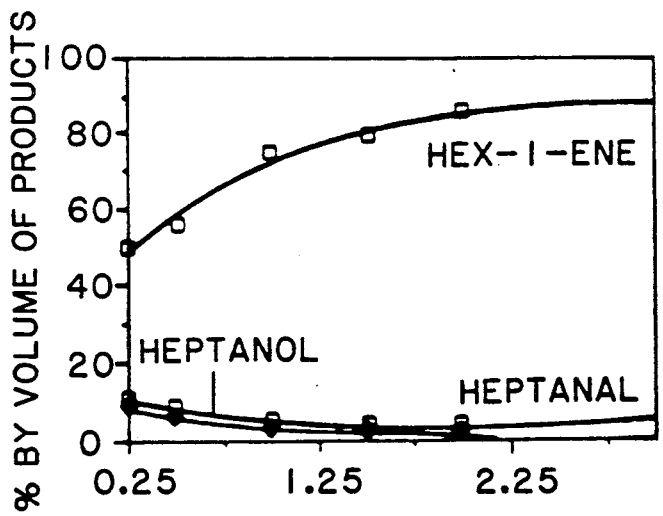

FIG. 7 shows, taking hex-1-ene as an example, the influence of the $CO/H_2$ ratio on the nature and the percentage of the main products obtained by GPC.

Figure 8:
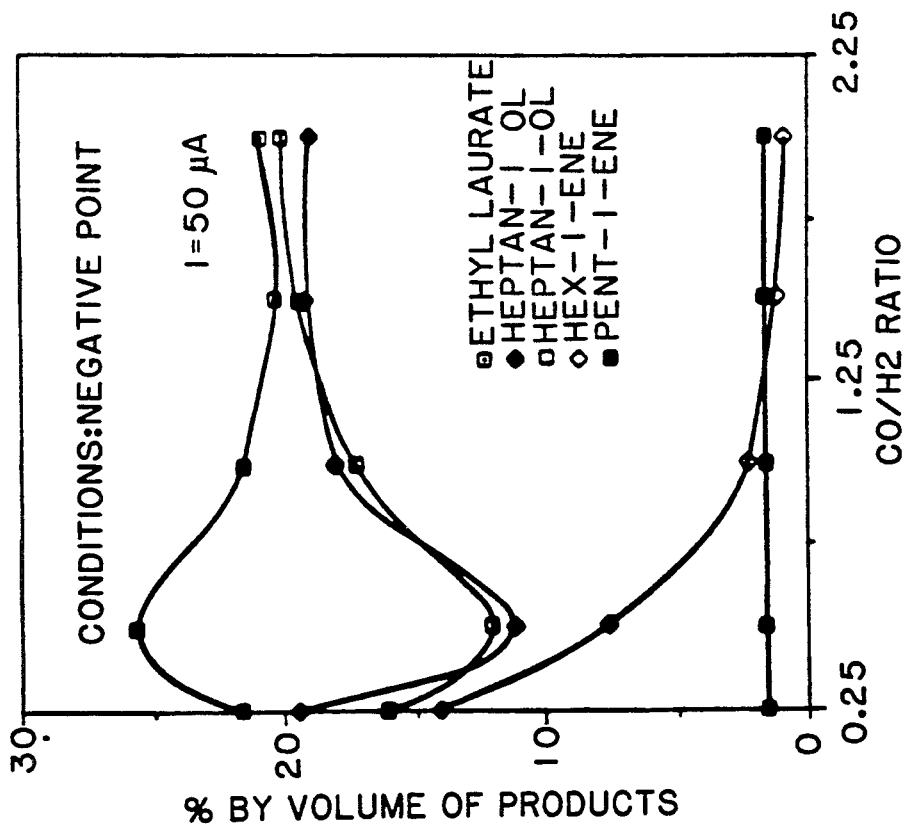

The operating conditions are:
$I = 50 \mu A$
$V = 18.5$ kV
time $t = 8.39$ minutes
$d_2 = 15$ mm; $d_1 = 8$ mm FIG. 8 shows the variation in the degrees of formation of the "oxo" products as a function of the $CO/H_2$ ratio (negative point discharge).

The operating conditions are:
$I = 50 \mu A$

Figure 9:
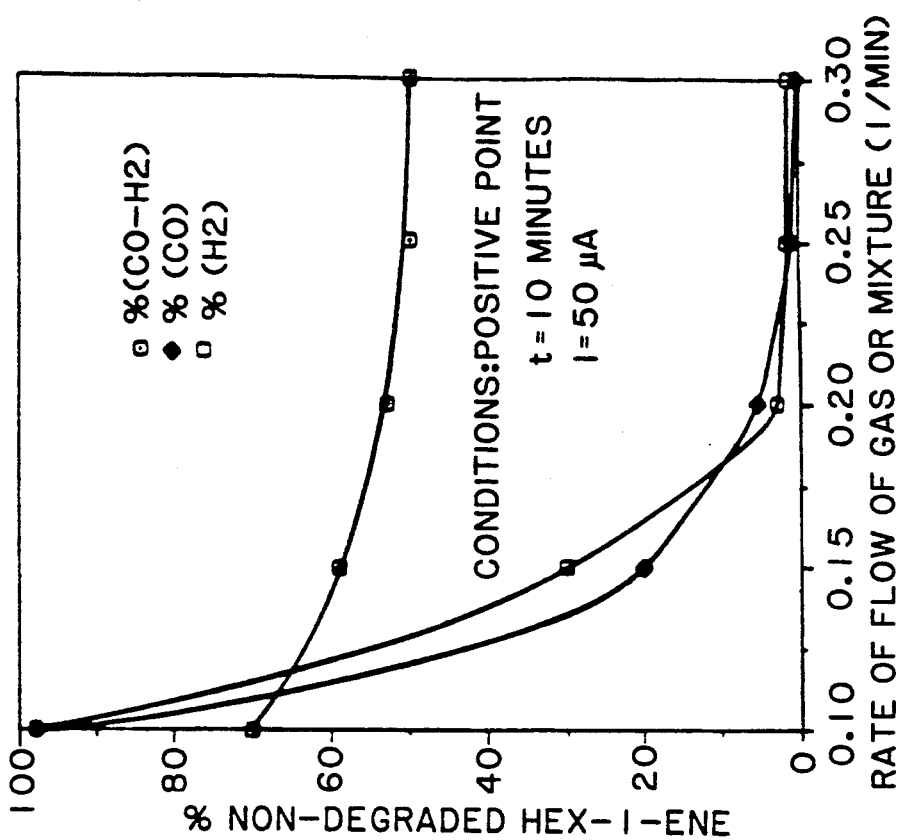

FIG. 9 shows the variation in the percentage of non-degraded hex-1-ene as a function of the flow rate of CO, $H_2$ or $CO + H_2$ (in the ratio 1/1).

The operating conditions are:
$I = 50 \mu A$
$t = 10$ minutes (positive point discharge).

Figure 10:
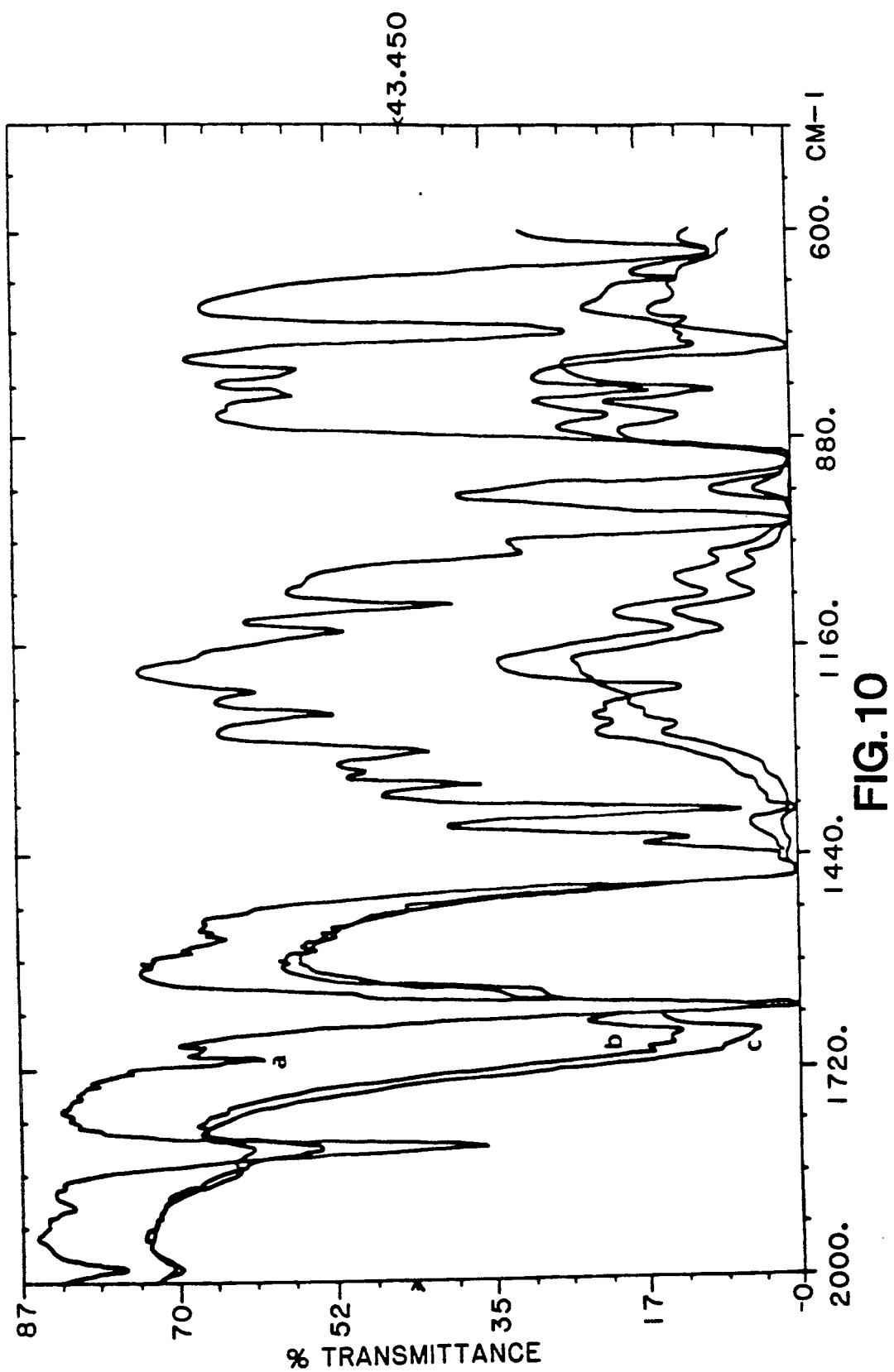

FIG. 10 shows infrared spectra showing the influence of the $CO/H_2$ ratio on the nature of the products formed (carbonyl functions); a) reference; b) $CO/H_2 = \frac{1}{2}$; c) $CO/H_2 = 1$.

Figure 11:
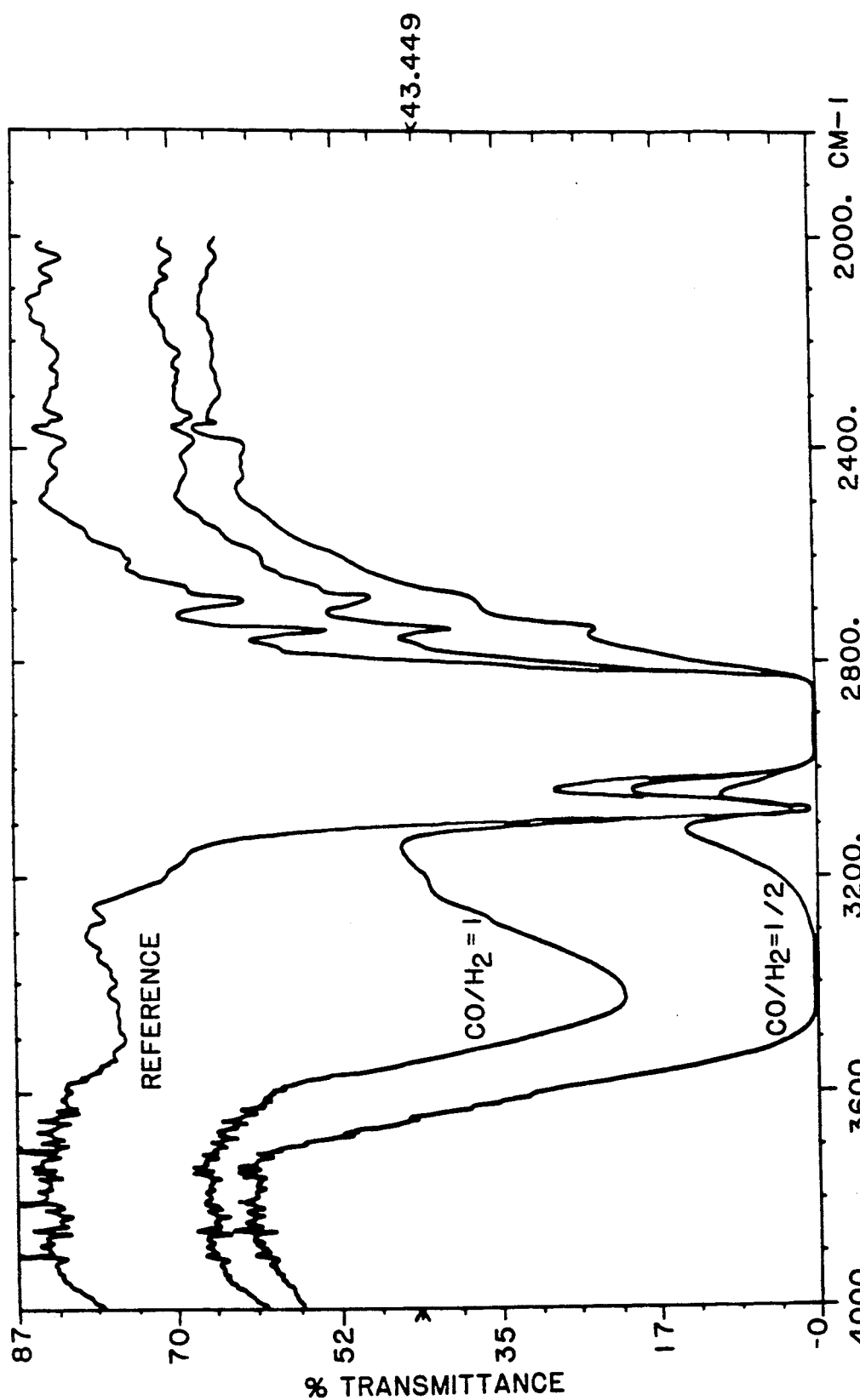

FIG. 11 shows the influence of the $CO/H_2$ ratio on the nature of the products formed (hydroxyl functions).

The operating conditions for obtaining the spectra are:
$I = 50 \mu A$
$t = 8.39$ minutes
$V = 17.5$ kV
$d_2 = 15$ mm; $d_1 = 8$ mm.

Figure 12:
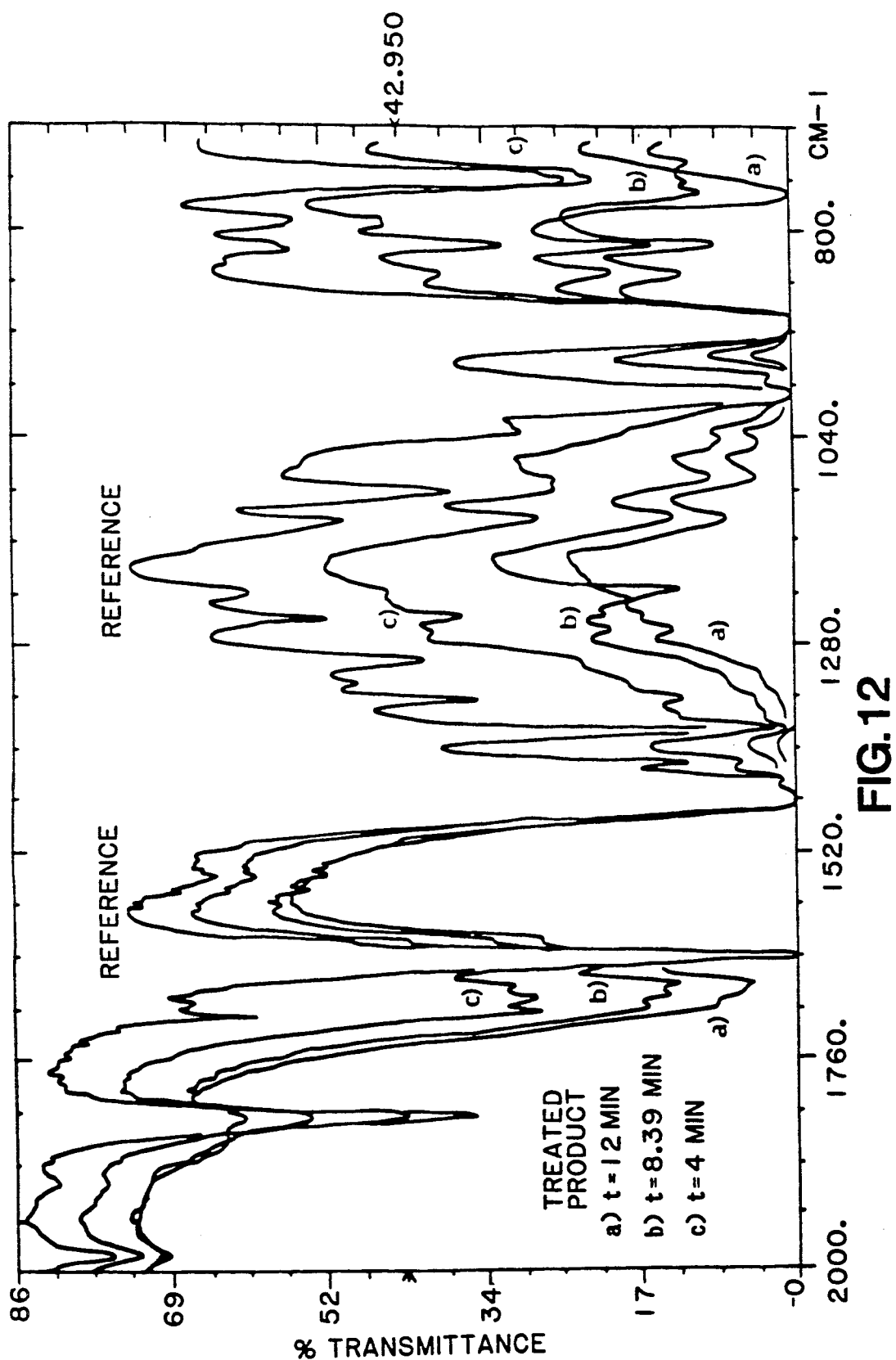

FIG. 12 shows infrared spectra showing the influence of the treatment time on the nature of the products formed (aldehydes, esters and carboxylic acids).

The operating conditions are:
$I = 50 \mu A$
$V = 21.5$ kV
$d_2 = 15$ mm; $d_1 = 8$ mm
a) $t = 12$ minutes; b) $t = 8.39$ minutes; c) $t = 4$ minutes.

Figure 13:
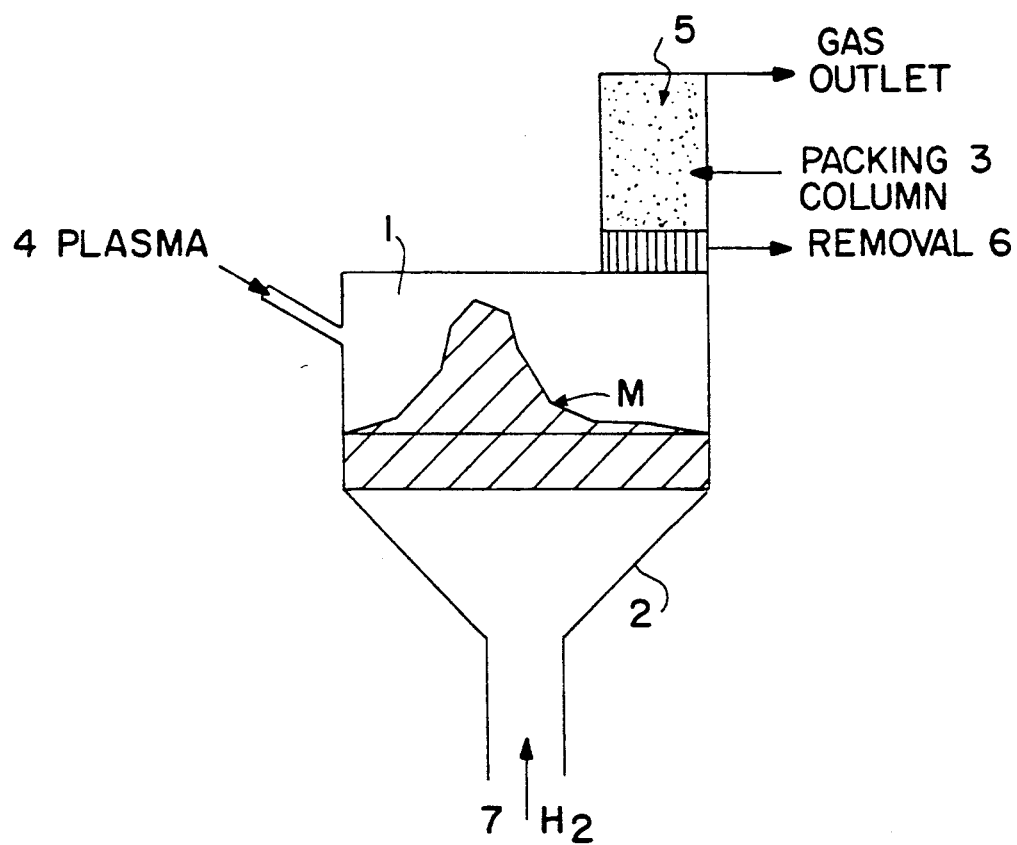

FIG. 13 shows a diagram of the installation containing a fluidized bed apparatus.

The choice of an unsaturated hydrocarbon substrate of the alkene type, that is to say hex-1-ene, subjected to an electric discharge occurring at a corona discharge in an adequate mixture of CO and $H_2$ with variable $CO/H_2$ ratios, enabled "oxo" products (aldehyde, alcohol, carboxylic acid, ester, etc.) to be prepared under very mild conditions.

In fact, it was shown that it is possible to synthesize "oxo" products by processes using the plasma route on the one hand, and on the other hand it was possible to determine the preponderant parameters enabling this production to be controlled, that is to say which are the predominant products and how the rates of formation of these products vary as a function of the various operating parameters of the reactor.

Figure 1:
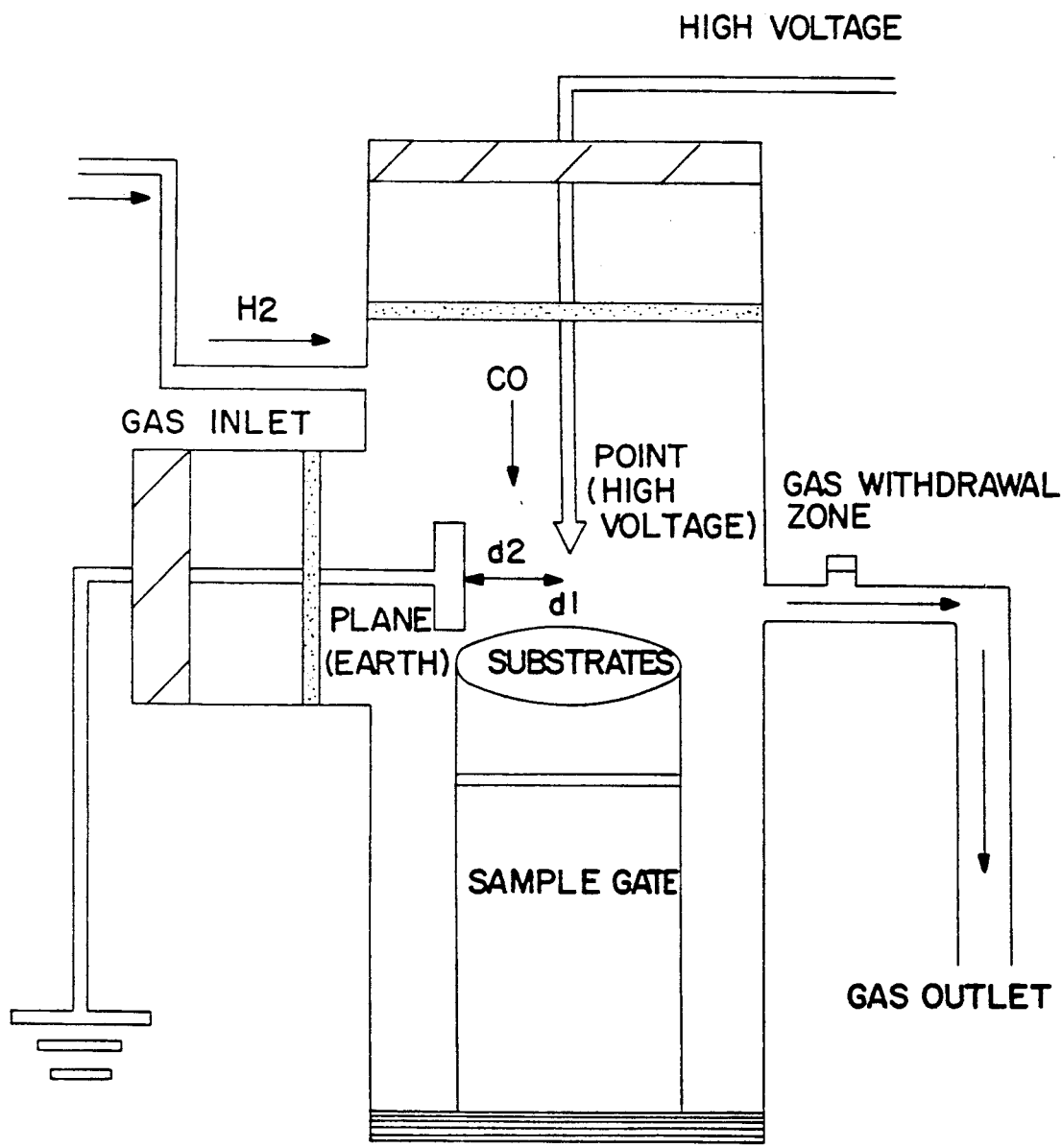
FIG. 1 shows the installation diagram of a plasma reactor of the point-plane corona discharge type usable in the process according to the invention.

The experiment was carried out at atmospheric pressure in a chemical plasma reactor of the point-plane corona discharge type. The diagram of the installation is shown in FIG. 1. In total, it comprises two parts:
 a high voltage generator supplying, in our particular case, a continuous maximum voltage of 30 kV, and the chemical reactor consisting of a quartz tube, having an internal diameter of 2.80 cm in the present case.

The feed flow rates of CO and $H_2$ are controlled by mass flow meters.

The reaction zone is contained between the point brought to the high voltage, the plane connected to earth and the walls of the quartz tube.

The liquid substrates, that is to say of hex-1-ene species, are introduced into the reactor via a sample gate arranged in the axis of the point and positioned at a distance from the point varying in the present case between 7 and 10 mm. The point is arranged parallel to the electrode consisting of the plane, which is earthed.

More precisely, the operating conditions using an apparatus as shown in FIG. 1 in the description which follows were as follows:
 point brought to the high voltage ($\pm$),
 plasma-producing gas: $CO + H_2$ in variable proportions,
 d1 (point-substrate distance): 7 to 10 mm,
 d2 (point-plane distance): 10 to 25 mm,
 current intensity: 20 to 70 $\mu A$,
 supply voltage: 10 to 25 kV,
 substrate used: hex-1-ene: $CH_3-(CH_2)_3-CH=CH_2$,
 analytical techniques: IR, GPC and Raman spectroscopy.

1) Principle of the reaction

The synthesis of "oxo" products in plasma phase can be regarded as a reaction proceeding in two steps:
 a first step is the activation of the reactants (CO and $H_2$) entering into the reactor. This activation produces both free radical and molecular species possessing high chemical reactivity. It is significant and increases with the intensity of the current injected into the discharge and the resulting electric field;
 a second step consists in the reaction of the activated species with the substrate (hex-1-ene) in accordance with an acido/basic reaction or nucleophilic and/or electrophilic addition reaction, which reaction is facilitated by the vacant boundary orbitals of the unsaturated bond of hex-1-ene.

The operating parameters which were studied are those relating to the functioning of the reactor, that is to say the current intensity, the treatment time of the substrate and the relative flow rates of $H_2$ and CO (variable CO/$H_2$ ratio).

2) Operating conditions

The reactor is washed with acetone in order to remove the carbon black deposits which have attached to the walls of the reactor and to the electrodes. It is then purged with argon. Hex-1-ene is introduced via the sample gate and the flow rates of CO and $H_2$ are monitored by mass flow meters. The CO is introduced through the hollow electrode consisting of the point and the hydrogen is introduced via the periphery of the reactor. The experiment is carried out at atmospheric pressure. The electric discharge is initiated and maintained at the chosen power throughout the period of the experiment.

The analysis of the products after reaction is carried out by Fourier transform IR spectrometry, in order to determine the functional groups resulting from the reaction, and by gas chromatography, in order to determine the carbon skeleton of the products obtained. Establishing a parallel between the results obtained by IR and those obtained by GPC enables us to follow the development of the various products from the discharge and to interpret the role of certain parameters.

With the aim of determining the chemical changes brought about by the discharge, the analysis of the products resulting from the reaction and that of the reference was carried out by infrared spectrometry. The product and the reference are recorded on the same spectrum; see, for example, FIG. 2.

The FTIR (Fourier transform IR) spectrum of the hex-1-ene reference shows absorption bands at 2920-2840 cm$^{-1}$, 1610-1650 cm$^{-1}$ and 138-1410 cm$^{-1}$, which are characteristic of the C—H, C=C and C—C bonds.

The spectrum of the treated hex-1-ene itself shows very intense supplementary absorption bands. Thus, bands are observed at 3404 cm$^{-1}$, 2920-2840 cm$^{-1}$, 1640 cm$^{-1}$ (less intense) and 1683-1720 cm$^{-1}$, which belong to the O—H($H_2O$ and/or alcohols), C—H, C=C, C—O and

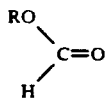

bonds.

The chemical bonds which it was possible to attribute to these bands are collated in Table III.

| Absorption limit in (cm$^{-1}$) | Bond | Intensity | Compounds functional groups |
|---|---|---|---|
| 3200-3600 | O—H | Strong and high | $H_2O$ or primary or secondary R—OH |
| 2500-3560 | O—H | Strong and high | Carboxylic acids |
| 3400 | O—H associated | Strong and high | Alcohols (dimers) or aldols |
| 3200-3300 | O—H | Strong and high | |
| 1683-1720 | C=O | Strong | Ketones, carboxylic |

-continued

| Absorption limit in (cm$^{-1}$) | Bond | Intensity | Compounds functional groups |
|---|---|---|---|
| | | | acids, unsaturated esters |
| 1640 | C=C | Strong | C=C conjugated with a C—C bond, or C=O |
| 1640 | O—H | Strong | H—O—H |
| 1280-1480 | C—O | Strong | Carboxylic acids, esters, alcohols |

3) Influence of the current intensity on the nature of the products formed

The current intensity was varied in a range ranging from 30 to 100 μA, the other parameters being kept constant: discharge time=8 min, distance (point-plane) =17 mm, distance (point-substrate)=8 mm, CO flow rate=0.10 l/min, $H_2$ flow rate=0.10 l/min.

Table 1 below shows the development of the various main products obtained as a function of the intensity (analysis carried out by GPC).

TABLE 1

| Conditions % X Products formed | $I_1 = 30$ μA X % products | $I_2 = 50$ μA X % products | $I_3 = 70$ μA X % products | $I_4 = 100$ μA X % products |
|---|---|---|---|---|
| Pent-1-ene | 1.96 | 1.50 | 1.43 | 1.31 |
| Hex-1-ene | 8.91 | 2.16 | 1.20 | 0.85 |
| Heptan-1-al | 15.92 | 18.33 | 14.53 | 11.91 |
| Heptan-1-ol | 13.93 | 17.56 | 17.20 | 12.19 |
| Ethyl laurate | 15.58 | 21.45 | 26.34 | 23.70 |

The analysis of the products by chromatography showed that heptan-1-al, heptan-1-ol and ethyl laurate form as predominant products. Pent-1-ene is also obtained as a by-product originating from cracking of hex-1-ene.

The examination of FIG. 6 and Table 1 relating to the development of the "oxo" products as a function of the current intensity shows that the degrees of formation of heptan-1-ol and of the aldehyde (heptan-1-al) increase and pass through a maximum and then decrease progressively as the current intensity increases. The decrease is much more pronounced in the case of the aldehyde than in the case of the alcohol (heptan-1-ol).

The curve relating to the aldol condensation product consisting of ethyl laurate ($C_{14}H_{28}O_2$) shows that the percentage of this product increases continually as the current intensity increases. With regard to the percentage of non-degraded hex-1-ene, this decreases very sharply when the current intensity increases. This development is corroborated by the aldol condensation reactions which take place as the aldehydes form.

For low current intensities (I<20 μA), an increase in the degree of formation of pent-1-ene is observed. When the current intensity increases, the percentage formation of pent-1-ene perceptively decreases.

It is evident from this analysis that the current intensity scale can be divided into two zones:

a first zone (I≦50 μA) where the percentages of "oxo" products increase with the current intensity (production zone);

a second zone (I≧50 μA) where the percentages of heptanol and heptanal decrease and the percentage of aldol condensation is seen to increase (zone of "degradation" of the aldehydes and alcohols). This difference in behaviour of the products can be exploited to improve the degree of formation of the desired products.

It will be noted that the values indicated for the current intensity are to be adapted as a function of the amount of substrate and of the size of the reactor used in the process. In the case under consideration, the amount of substrate treated was 3 ml in our experiments.

The IR spectrum in FIG. 5 relating to variations in the electric current shows that the amplitude of the absorption bands and the products treated increase very sharply as the current intensity increases. On the other hand, the amplitude of the absorption band at 1640 $cm^{-1}$ characterizing the double bond decreases very sharply when the current intensity increases. The increase in the intensity of the band at 1720 $cm^{-1}$ (C=O) and the decrease in the band at 1640 $cm^{-1}$ (C=C) show that the carboxyl group attaches to the double bond of the alkene (hex-1-ene).

4) Influence of the inter-electrode distance

Figure 2:
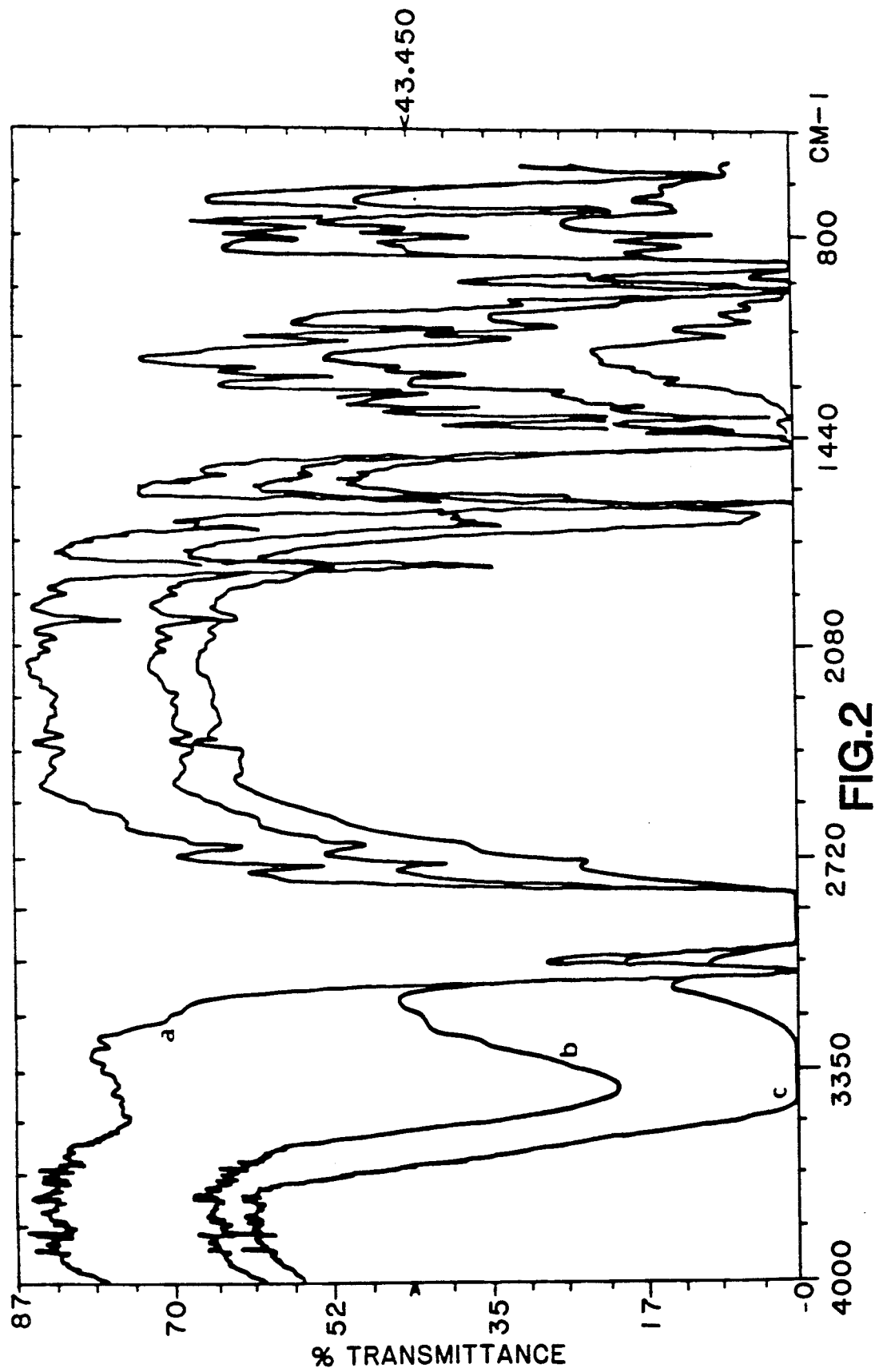
FIGS. 2 to 5 show infrared spectra.

The comparison of the spectra in FIGS. 2 to 4 obtained for inter-electrode distances of 7, 8, 10, 13 and 17 mm shows that the intensity of its bands increases as a function of the inter-electrode distance.

5) Influence of the CO/$H_2$ ratio on the nature of the products formed

The study of the influence of the relative flow rates of CO and $H_2$ on the nature and the percentages of the products formed was carried out keeping the current intensity constant (I is 50 μA). The analysis of the liquid products collected during the experiments is carried out by IR spectrometry and by chromatography.

The measurements and the analyses enabled the variations in the proportions of non-degraded hex-1-ene and those of heptan-1-al, heptan-1-ol, ethyl laurate and pent-1-ene resulting from the degradation of hex-1-ene to be plotted as a function of the CO/$H_2$ ratio (for a given intensity); the results are given in Table 2 and in FIG. 7.

Table 2 below shows the operating conditions and the development of the various main products obtained as a function of the CO/$H_2$ ratio rapid and can take place without catalyst, which is confirmed by our results. However, it should be noted that the discrepancy between theory and our results appears to be established when the CO/$H_2$ ratio is ½. This example deserves particular attention because it runs counter to the generally accepted theory, according to which the increase in the flow rate of hydrogen relative to that of carbon monoxide is reflected in an increase in the percentage of alcohol to the detriment of the aldehydes. The curves relating to heptan-1-ol and heptan-1-al show a minimum for CO/$H_2$=½ (see FIG. 8). The fact that, in the present case, the increase in the flow rate of hydrogen instead of increasing the percentage of alcohols decreases this to the benefit of the aldol condensation products shows that this parameter is highly inadequate for explaining on its own the percentage of alcohol formation.

6) Influence of the CO and $H_2$ flow rates

To specify the role of each of the reactants CO and $H_2$, the variations in the percentages of non-degraded hex-1-ene has been plotted as a function of the flow rates of CO, $H_2$ and CO+$H_2$ mixture, for a given current intensity (I=50 μA). These results are given in FIG. 9.

These curves show that the percentages of nondegraded hex-1-ene decrease when the flow rates of CO and $H_2$ increase. This decrease is much more pronounced in a CO atmosphere and in a CO+$H_2$ mixture than in a $H_2$ atmosphere. This low percentage of hex-1-ene in a $H_2$ atmosphere relative to pure CO and CO+$H_2$ atmospheres can be explained hydrogen flow rate at constant current causes a lowering in the discharge voltage. Thus, keeping the current constant (I=50 μA), increasing the hydrogen flow rate from 0.1 l/min to 0.30 l/min causes the voltage to change from 28 kV to 16 kV, which explains the ineffectiveness of $H_2$ in the corona discharge degradation of hex-1-ene.

The search for the explanation relating to the decrease in alcohols formed can be examined in terms of heterogeneous phase catalysis in general and of the specific nature of plasma phase catalysis in particular.

TABLE 2

| Conditions % X Products formed | CO/$H_2$ = 2 X % products | CO/$H_2$ = 1 X % products | CO/$H_2$ = ½ X % products | CO/$H_2$ = ⅓ X % products | CO/$H_2$ = ¼ X % products |
|---|---|---|---|---|---|
| Pent-1-ene | 1.62 | 1.50 | 1.61 | 1.91 | 1.63 |
| Hex-1-ene | 1.40 | 2.16 | 8.38 | 11.60 | 14.10 |
| Heptan-1-al | 19.14 | 18.33 | 10.85 | 16.36 | 19.51 |
| Heptan-1-ol | 19.83 | 17.56 | 12.13 | 13.25 | 16.80 |
| Ethyl laurate | 20.54 | 21.45 | 25.32 | 23.11 | 22.76 |

These curves indicate that the percentage of nondegraded hex-1-ene decreases sharply when the CO/$H_2$ ratio increases. The proportion of pent-1-ene formed remains constant whatever the variation in the CO/$H_2$ ratio. The degrees of formation of heptan-1-ol and of heptan-1-al show a minimum for a CO/$H_2$ ratio of ½ and then increase in the same direction to stabilize at about a value of 20%. In parallel, the ethyl laurate content increases very sharply when the CO/$H_2$ ratio increases, passes through a maximum for CO/$H_2$=½ and then decreases to stabilize at about a value which is constant whatever the variation in the ratio (see FIG. 8). Thus, the value of CO/$H_2$=½ constitutes a ratio enabling rationalization of the synthesis of the aldol condensation products to the detriment of the "oxo" alcohols and aldehydes. Theory shows that the reaction leading to aldol condensation products being obtained is very On the basis of this hypothesis, a parallel study by IR spectrometry was able to show a very sharp increase in the absorption bands at 3404 $cm^{-1}$, 1683-1720 $cm^{-1}$ and 1280-1480 $cm^{-1}$ (see FIGS. 10 and 11).

The IR spectra in FIGS. 10 and 11 show that these bands increase very sharply when the CO/$H_2$ ratio decreases, reflecting the formation of alcohols, carboxylic acids or ester and water.

The presence of water shows that the aldehyde formed can undergo an aldolization and a crotonization to give unsaturated aldehydes in accordance with the following reaction scheme:

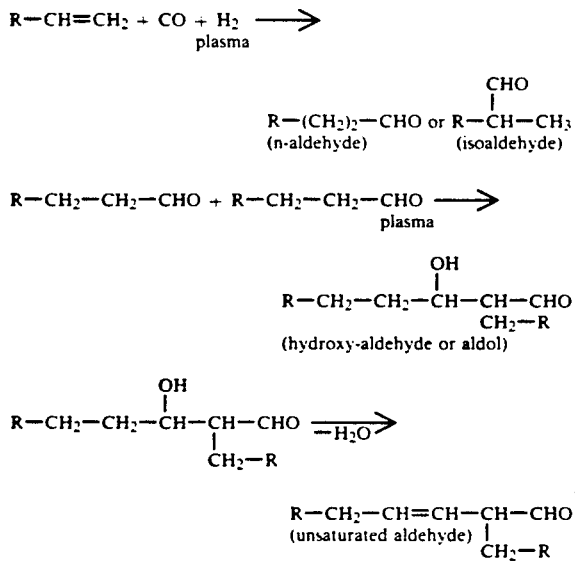

In conclusion, the decrease in the CO/H$_2$ ratio very greatly increases the formation of the "oxo" aldehydes and alcohols, which easily convert to aldols.

7) Influence of the discharge time on the percentaqes of the products formed

The study on the influence of treatment on the percentages of the products was carried out for a given CO/H$_2$ ratio of $\frac{1}{2}$ and for a given current intensity (I = 50 μA).

In order to restrict the phenomena of cracking and evaporation of the substrate, we carried out tests of very short duration (tests of 5.8 and 12 minutes).

The analysis of the IR spectra of the treated substrates shows that the absorption bands at 3427 cm$^{-1}$ characterize the O—H bonds and those located at 1683 cm$^{-1}$ (C=O bonds) increase as the treatment time increases. However, a very pronounced growth of the bands at 3427 cm$^{-1}$ to the detriment of the bands at 1682 cm$^{-1}$ is observed. The spectra in FIG. 12 relating to the reference hex-1-ene and to the products treated for 4; 8.39 and 12 minutes represent the different variations.

All of these results show the importance of the duration of the discharge with regard to obtaining the different products.

In fact, the flow of activated CO towards the material depends on the energy density of the relative species created in the discharge. Now, the two processes (cracking and fixation of CO) depend very greatly on the time for which the material is treated by the plasma, that is to say the elementary reaction mechanisms which establish the overall development of the subsequent reactions. Consequently, a minimum treatment time is necessary for the initiation of the discharge and obtaining a product.

In particular, for an amount of substrate of 3 ml, the minimum treatment time is 4 minutes.

8) Installation with a thermal plasma reactor and an apparatus for chilling by fluidized bed FIG. 13 is a diagrammatic view of an installation with a fluidized bed apparatus implemented in accordance with one variant of the invention.

In FIG. 13, the installation comprises a fluidized bed apparatus comprising a chamber 1 of parallelepiped general shape, the bottom 2 of which, which has a shape widening towards the top, is connected at the level of its lower part to means for the injection of a fluidization gas.

A tubular reactor 3 is connected to the upper part of the chamber 1 in such a way that the reactor 3 is in communication with the interior of the chamber, and a plasma torch 4, containing inductors in the conventional manner, passes through a side wall of the chamber 1 so as to inject a plasma into a mass M of particles arranged in the chamber 1. The particles of the mass M are intended to be fluidized to form a bed of the gushing type by the fluidization gas 7 penetrating into the chamber.

The fluidized particles M, for example Al$_2$O$_3$ particles, have a grain size such that 43% by weight of the spheres have a diameter of between 500 and 350 μm and 57% by weight have a diameter of between 630 and 500 μm. This grain size proportion permits gushing fluidization without entraining particles in the chamber 1 up to a fluidization gas flow rate of the order of 50 l/min.

The tubular reactor 3 consists of a packing column operating in accordance with the principle of absorption columns. The outlet from the tubular reactor 3 is connected to means for recovery and fractionation by condensation of the exiting hydrocarbon products 6.

These means can comprise, in the vicinity of the outlet of tubular reactor 3, a water condenser, to which a solid carbon dioxide trap and a liquid nitrogen trap are connected successively. Downstream, the liquid nitrogen trap can be connected to a washing bottle, in which a reduced pressure is created by means of a pump.

In operation, the installation which has just been described functions as follows. The mass M of solid particles, of defined diameter, are fluidized to a gushing bed, having the shape of a fountain and falling back towards the walls of the chamber, by the constant flow of a fluidization gas consisting of hydrogen.

The plasma torch 4 injects a plasma containing a CO+H$_2$ mixture laterally into the fluidized bed of particles, where, on mixing and cooling, it transfers some of its heat to the particles, which exchange this heat with the fluidization gas.

The reaction takes place in the tubular reactor 3. The hydrocarbon products 5 to be treated circulate in the column in counter-current to the current of the mixture of activated reactants.

The hydrocarbon products 6 leaving the tubular reactor 3 are then fractionated as a function of their condensation point in the water condenser, in the solid carbon dioxide trap and in the liquid nitrogen trap for the lightest products.

The plasma torch operates, for example, at a frequency of 5 MHz at a power of up to 9 kW and an efficiency of 50%. The flow rate of plasma-producing gas is, for example, 40 to 50 l/min.

We claim:

1. Process for the synthesis of "oxo" products or their derivatives consisting of hydrocarbon compounds containing groups selected from carbonyl groups, hydroxyl groups and both carbonyl and hydroxyl groups, characterized in that a hydrocarbon substrate containing an unsaturation, such as an alkene, is reacted with reactants consisting of a mixture of hydrogen and carbon monoxide, the reaction taking place after bring the substrate into contact with the neutral activated species of the mixture of reactants activated to the plasma state.

2. Process according to claim 1, characterized in that an alkene is reacted to obtain a mixture containing the aldehyde and the alcohol resulting from the fixation on the double bond of the alkene of, respectively, a group

or its group

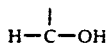

obtained by reduction, or only one of these two components by separating it from the mixture.

3. The process according to claim 1, characterized in that the activation of the hydrogen/carbon monoxide mixture takes place in a plasma reactor, the substrate being brought into contact with the activated mixture outside the activation zone of the plasma.

4. Process according to claim 3, characterized in that the substrate and the reactants are introduced into the reactor at atmospheric pressure and at a temperature close to ambient temperature.

5. The process according to claim 1, characterized in that the ratio of the $CO/H_2$ volume flow rates is greater than 1.

6. The process according to claim 5, characterized in that the ratio of the $CO/H_2$ volume flow rates is of the order of ½.

7. The process according to claim 3, characterized in that the plasma reactor is of the point-plane corona discharge type, the point being arranged parallel to the plane electrode, and the substrate is introduced into the reactor in the acis of the point and below the activation zone, wich is located between the point and the plane.

8. Process according to claim 7, characterized in that the point electrode is positively charged and the plane electrode is connected to earth.

9. Process according to one of claims 7 or 8, characterized in that the carbon monoxide is introduced at the level of the point electrode and the hydrogen is introduced at the periphery of the reactor.

10. Process according to one of claims 1 to 6, characterized in that the plasma reactor is of the thermal plasma type, the activated $CO+H_2$ mixture being subjected, after activation, to chilling by a fluidized bed of particles by a stream of hydrogen gas at a temperature of 20° to 150° C. before being brought into contact with the substrate to be treated.

11. Installation, usable in the process according to one of claims 1 to 8, consisting of a plasma reactor of the point-plane corona discharge type, characterized in that it comprises one or more hollow point electrodes through which the reactor is fed with carbon monoxide gas, the point electrode being arranged parallel to the plane electrode, the hydrogen being introduced at the periphery of the reactor and the liquid hydrocarbon substrate being placed under the point in its axis at a point-substrate distance smaller than the point-plane distance.

12. Installation, usable for carrying out the process according to claim 10, characterized in that it comprises a high-frequency plasma reactor producing a $CO+H_2$ plasma torch injected laterally into a chamber of a fluidized bed apparatus, a tubular reactor of the packing column type being connected to the outlet of the said chamber, in which the substrate circulates in counter-current to the flow of activated $CO+H_2$ mixture.

13. Process according to claim 3 characterized in that the substrate and the reactants are introduced into the reactor at a temperature close to ambient temperature.

* * * * *

UNITED STATES PATENT AND TRADEMARK OFFICE
CERTIFICATE OF CORRECTION

PATENT NO. : 5,122,245
DATED : June 16, 1992
INVENTOR(S) : Avaly Doubla, et al

It is certified that error appears in the above-indentified patent and that said Letters Patent is hereby corrected as shown below:

Column 1, line 14, after "hydrogen" insert --.--

Column 10, line 31, after "explained" insert --in terms of electric power. In fact, the increase in the--

Signed and Sealed this

Eighth Day of February, 1994

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,122,245
DATED : June 16, 1992
INVENTOR(S) : Doubla et al.

It is certified that error appears in the above-indentified patent and that said Letters Patent is hereby corrected as shown below:

<u>ON THE TITLE PAGE:</u>

[73] Assignees change "Electricite De France" to
--Electricite De France (Service National)--.

Signed and Sealed this

Second Day of April, 1996

Attest:

BRUCE LEHMAN

Attesting Officer     Commissioner of Patents and Trademarks